United States Patent [19]
Littleford, deceased et al.

[11] Patent Number: 4,834,093
[45] Date of Patent: May 30, 1989

[54] DILATION CATHETER AND METHOD

[76] Inventors: Phillip O. Littleford, deceased, late of Winter Park; by H. Richard Bates, personal representative, 322 E. Central Blvd., Orlando, both of Fla. 32801

[21] Appl. No.: 825,157

[22] Filed: Feb. 3, 1986

[51] Int. Cl.$^4$ ............................................. A61N 5/06
[52] U.S. Cl. .................................. 128/303.1; 128/398
[58] Field of Search ........... 128/303.1, 303.11–303.15, 128/395–398

[56] References Cited

U.S. PATENT DOCUMENTS

| | | | |
|---|---|---|---|
| 3,308,823 | 3/1967 | Peterson | 128/303.1 |
| 3,590,232 | 6/1971 | Sadowski | 128/303.1 |
| 3,961,621 | 6/1976 | Northered | 128/303.1 |
| 4,273,109 | 6/1981 | Enderby | 128/303.1 |
| 4,273,128 | 6/1981 | Lary | 128/344 |
| 4,420,407 | 9/1984 | Hussein | 128/303.1 |
| 4,445,892 | 5/1984 | Hussein et al. | 128/303.1 |
| 4,512,762 | 4/1985 | Spears | 128/303.1 |
| 4,564,024 | 1/1986 | Crittenden et al. | 128/303.1 |
| 4,631,052 | 12/1986 | Kensey | 128/305.1 |
| 4,681,104 | 7/1987 | Edelman | 128/303.1 |

FOREIGN PATENT DOCUMENTS

| | | | |
|---|---|---|---|
| 153847 | 9/1985 | European Pat. Off. | 128/303.1 |
| 2826383 | 12/1979 | Fed. Rep. of Germany | 128/303.1 |
| 8404879 | 12/1984 | World Int. Prop. O. | 128/303.1 |

Primary Examiner—Lee S. Cohen
Assistant Examiner—David Shay

[57] ABSTRACT

An apparatus and method for opening an obstructed tubular passageway in the human body. A first catheter having a distal end dimensioned to pass freely along a tubular passageway is guided to the obstruction. A proximal end of the first catheter is adapted to extend outside the human body and is coupled to a source of coherent radiation. Coherent radiation is transmitted from the source to the distal end of the first catheter to permit the coherent radiation to be directed against the obstruction to bore a passageway through the obstruction. After a passageway has been bored through the obstruction, the first catheter is removed from the tubular passageway. A second catheter having a distal end dimensioned to pass freely along the tubular passageway, a proximal end adapted to extend outside the human body, and a peripheral elastic expandable zone spaced from the distal end is guided into the passageway through the obstruction. The expandable zone of the second catheter is expanded to increase the passageway through the obstruction. The second catheter is then removed from the tubular passageway.

23 Claims, 3 Drawing Sheets

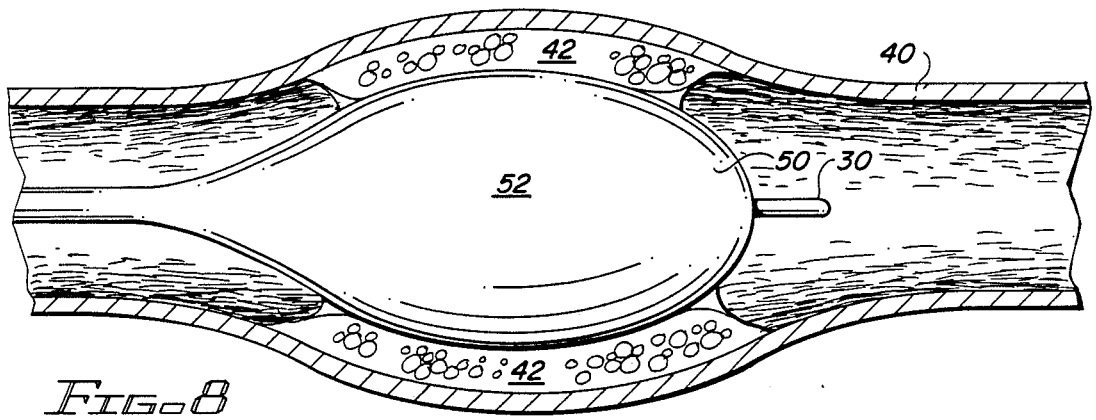
FIG.-7
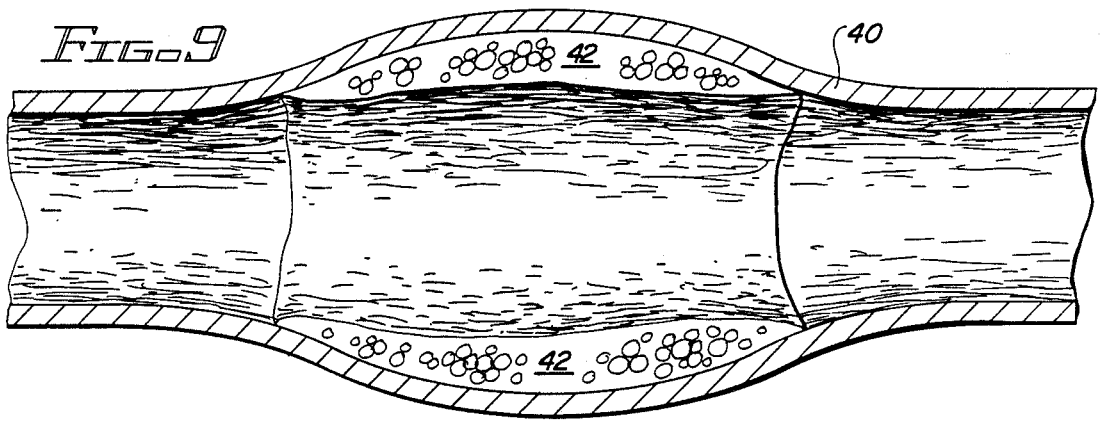
FIG.-8
FIG.-9
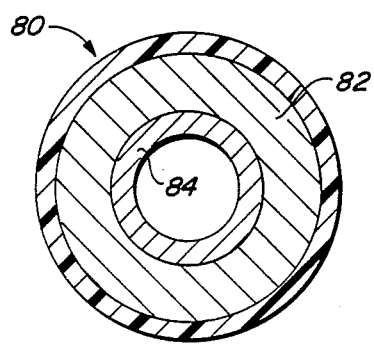
FIG.-12

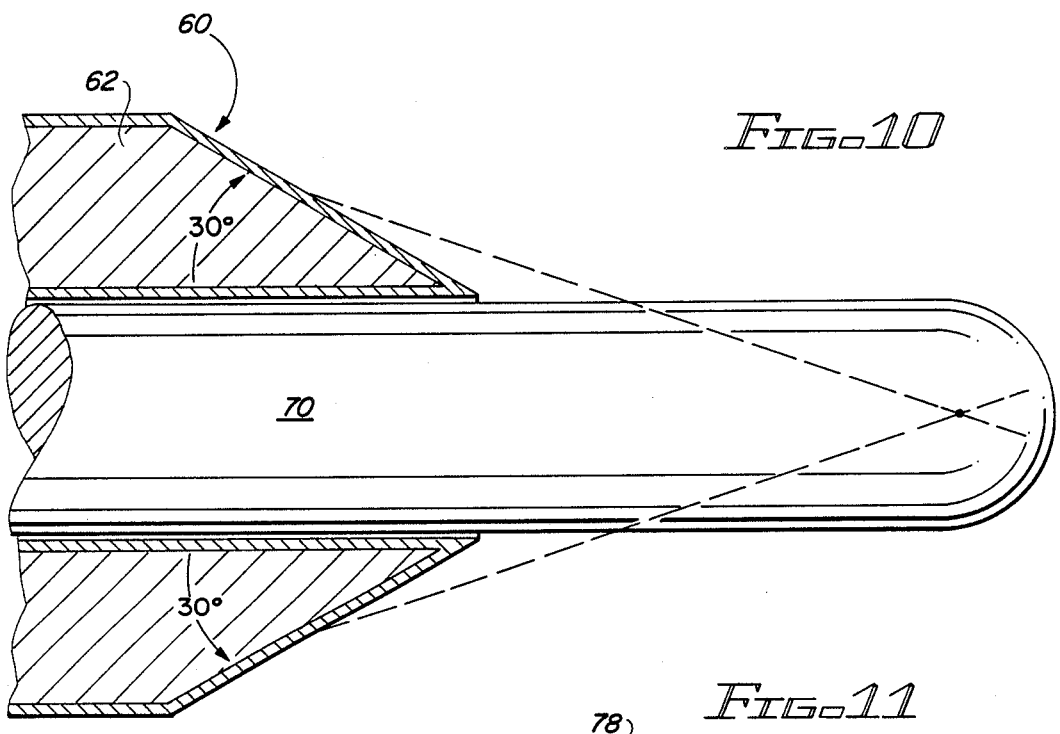
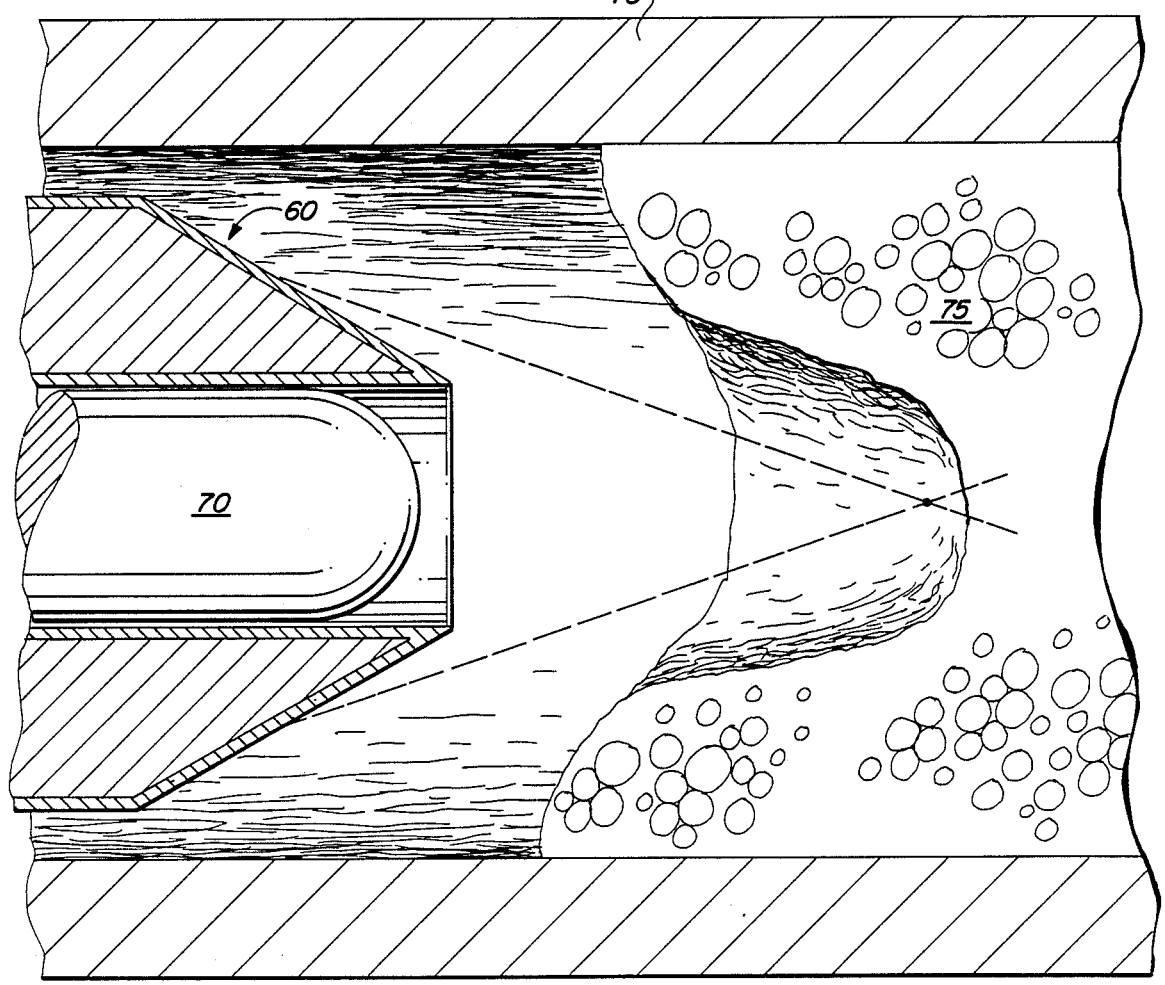

DILATION CATHETER AND METHOD

BACKGROUND OF THE INVENTION

This invention relates to catheters and methods for dilating blood vessels to open occlusions and, more particularly, to coherent light transmitting dilation catheters and related methods.

Numerous catheter devices have been proposed for use in blood vessels for opening occlusions. The occluding material, commonly referred to as plaque, is often a soft jelly-like substance. When the plaque is a soft jelly-like substance, balloon percutaneous translumenal coronary angioplasty (PTCA) is frequently effective in reducing the occlusion. With PTCA, a catheter having expandable walls is inserted into the femoral artery of a patient, passes through the femoral artery into a coronary artery and penetrates the soft plaque. With the catheter in place, its walls are expanded to dilate and disperse the plaque over the interior surface of the blood vessel to open the occlusion. The catheter is then deflated and removed from the blood vessel.

Sometimes the plaque is hard and calcified rather than soft and jelly-like. If the plaque is calcified, a catheter might not be able to penetrate the plaque. In such a situation, PTCA cannot be used to open the occlusion.

Various proposals have been made for combining fiber optic bundles with a catheter for use within a blood vessel. These prior devices direct coherent light, eg., laser light, to calcified plaque within blood vessels to ablate the occlusions. One concern accompanying the use of laser energy to remove occlusions within blood vessels is perforating the walls of the blood vessels with the laser energy. Prior patents pertaining to catheters utilizing coherent energy include: U.S. Pat. No. 4,207,874 to Choy; U.S. Pat. No. 4,418,688 to Loeb; and U.S. Pat. No. 4,445,892 to Hussein et al.

The patent to Choy discloses a catheter having expandable walls for retaining the catheter within a lumen while a laser is disintegrating an occlusion. The patent to Hussein discloses a dual balloon catheter device with two spaced and expandable balloons for providing an isolated operating region between the two balloons within a blood vessel. In that device, the balloons are positioned on either side of an occlusion and the occlusion is obliterated by laser energy. The plague is then removed from the isolated region by way of a suction tube.

Other patents pertaining to catheters include: U.S. Pat. No. 3,837,347 to Tower; U.S. Pat. No. 4,261,339 to Hanson et al; U.S. Pat. No. 4,346,698 to Hanson et al; U.S. Pat. No. 4,349,029 to Mott; U.S. Pat. No. 4,404,971 to LeVeen et al; U.S. Pat. No. 4,423,725 to Baran et al; and U.S. Pat. No. 4,335,723 to Patel.

It is an object of the present invention to provide an apparatus for boring a passageway through an occlusion within a blood vessel so that a catheter may pass through the passageway.

It is a further object of the present invention to provide means which allows a balloon catheter to be placed within a passageway for dilating an occlusion.

SUMMARY OF THE INVENTION

The present invention teaches an apparatus and method for opening an occlusion which is within a passageway in a human body. The apparatus comprises a catheter having a distal end dimensioned to pass freely along the passageway and a proximal end adapted to extend outside the human body during use. A source of coherent radiation is coupled to the proximal end of the catheter. The catheter is provided with means for transmitting the coherent radiation from the source to the distal end of the catheter to permit the coherent radiation to be directed against the occlusion to bore a tunnel through that obstruction so that a catheter may pass through the tunnel. The apparatus is further provided with means for guiding the distal end of the catheter to the obstruction, and thereafter through the obstruction as the laser energy forms the tunnel.

Preferably, the catheter has a longitudinal lumen with the guiding means comprising a guidewire dimensioned to pass through the lumen. Flexible fiber optic rods extend generally longitudinally along the catheter and generally parallel with the lumen.

Coherent radiation is transmitted from the source to the distal end of the catheter to permit the coherent radiation to be directed against the occlusion to bore the tunnel through the occlusion. Only small amounts of the plaque forming the occlusion are removed at a time. As each small portion of plaque is removed, the guidewire is pushed against the occlusion within the bored tunnel. The guidewire is incrementally pushed against the occlusion and coherent radiation is sequentially directed to the occlusion until a small tunnel is bored completely through the occlusion. Once a through tunnel has been made, the catheter is removed from the passageway with the guidewire left in place. A balloon catheter having a peripheral elastic expandable zone spaced from the distal end is passed over the guidewire and the expandable zone is placed into the tunnel through the obstruction. The expandable zone of the balloon catheter is then expanded to dilate the tunnel through the occlusion. Once the tunnel has been dilated, the balloon catheter is removed from the passageway. Thus, the plaque is prevented from obstructing the passageway.

BRIEF DESCRIPTION OF THE DRAWINGS

The foregoing and other objects, features and advantages of the invention will become more apparent by reference to the accompanying drawings and the following detailed description taken in conjunction with the drawings in which:

FIG. 7 illustrates a balloon catheter over the guidewire of FIG. 6;

FIG. 8 illustrates an inflated balloon catheter dilating a blood vessel to open an occlusion and FIG. 9 illustrates an opened occlusion;

FIG. 10 illustrates a cross-sectional view of a laser catheter having cleavage planes for focusing coherent radiation onto a guidewire;

FIG. 11 illustrates a cross-sectional view of the catheter of FIG. 10 focusing coherent radiation on an occlusion; and FIG. 12 illustrates a cross-sectional view of a laser catheter having a single fiber optic rod with a longitudinal lumen through the rod.

DETAILED DESCRIPTION

Figure 1:
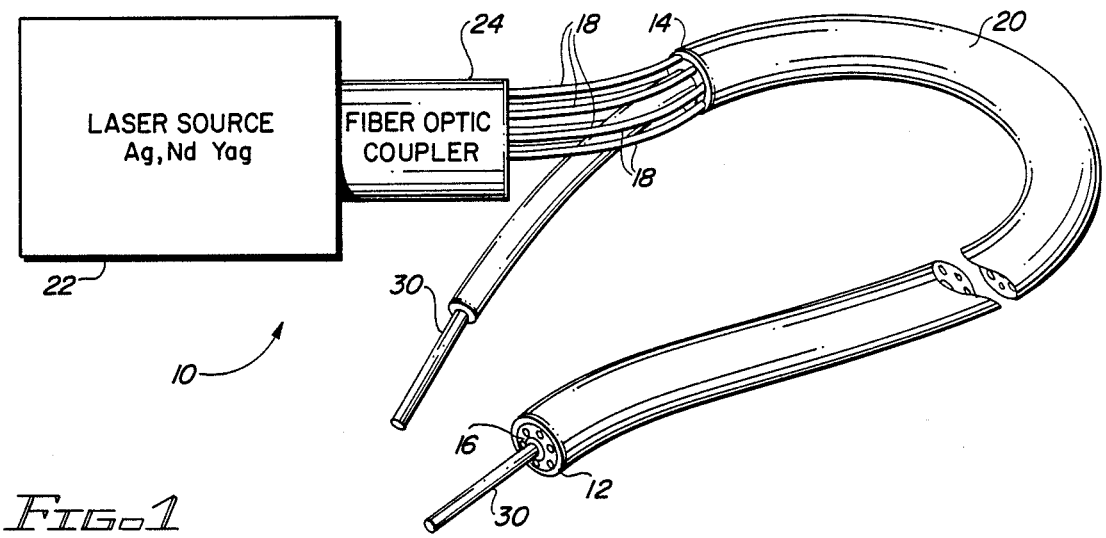
FIG. 1 illustrates a schematic view of a laser catheter in accordance with the present invention.
Figure 2:
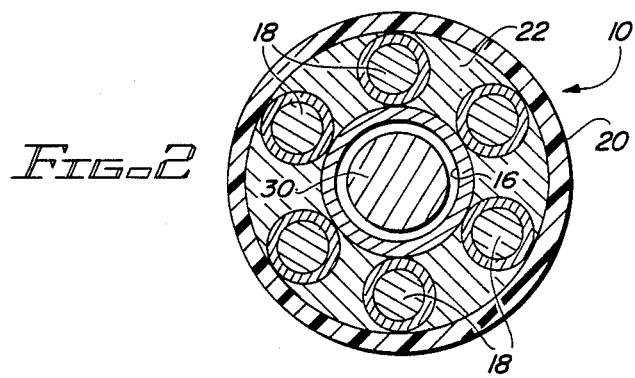
FIG. 2 illustrates a cross-sectional view of a laser catheter in accordance with the present invention.

Reference is made to FIGS. 1 and 2 which illustrate a laser catheter 10 in accordance with the present invention. The laser catheter 10 has a distal end 12 dimensioned to pass freely along a blood vessel in a human body and a proximal end 14 adapted to extend outside the human body during use. A longitudinal lumen 16 extends along the center of the catheter 10. The lumen 16 is dimensioned to permit a guidewire 30 to pass through the lumen 16. A plurality of flexible fiber optic rods 18 extend longitudinally along the catheter 10 and are disposed about the lumen 16. Preferably, Teflon tubing 20 overlays the catheter 10 to reduce friction as the catheter 10 is placed through a blood vessel.

A laser source 22, well known in the art, provides coherent radiation to the fiber optic rods 18. The laser source 22 is coupled to the fiber optic rods 18 by way of a fiber optic coupler 24, well known in the art. Preferably, the laser source 22 use an argon laser energy medium or infrared or neodymium-yttrium, aluminum-garnet (NdYag) medium.

As shown in FIG. 2, the fiber optic rods 18 are disposed about the lumen 16 by a non-toxic binder 22, well known in the art. Lumen 16 is dimensioned to allow the catheter 10 to pass freely over the guidewire 30.

Figure 3:
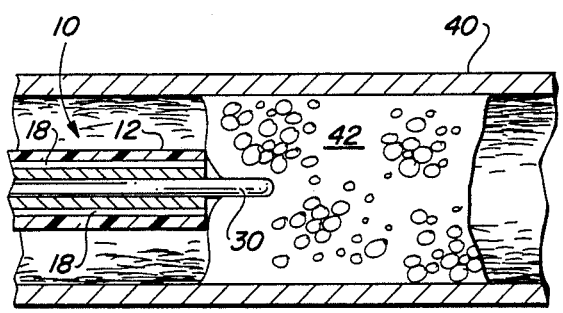
FIG. 3 illustrates a laser catheter and guidewire abutting an occlusion.

Referring to FIG. 3, the catheter 10 and the guidewire 30 are introduced into a blood vessel. With the aid of the guidewire 30, the distal end 12 of the catheter 10 is guided to an occlusion formed by plaque 42 within the blood vessel 40. Known fluoroscopic techniques are used to visually guide the catheter 10 to the occlusion. The guidewire 30 is pushed into the plaque 42 while keeping the guidewire 30 substantially parallel to the blood vessel 40. With the guidewire 30 pushed against the plaque 42, the risk of perforating the wall of the blood vessel 40 is reduced since the coherent radiation is directed parallel to the guidewire 30.

Figure 4:
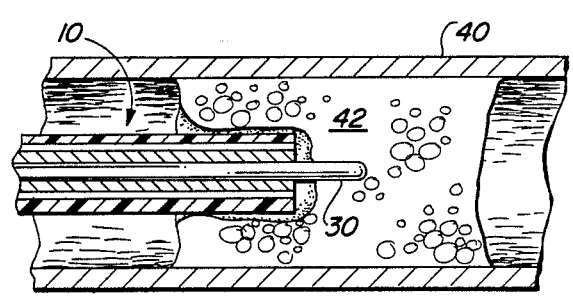
FIG. 4 illustrates a partially bored tunnel within an occlusion.
Figure 5:
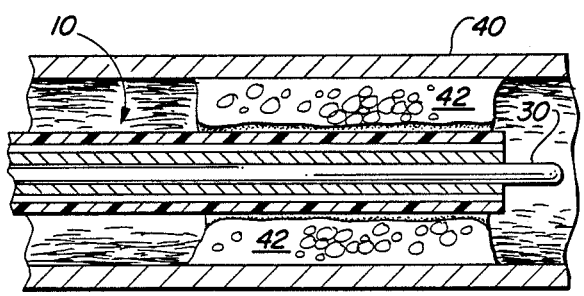
FIG. 5 illustrates a tunnel bored entirely through an occlusion.

FIGS. 4 and 5 illustrate the catheter 10 boring a tunnel through the plaque 42. The guidewire 30 is pushed against the plaque 42 and a small amount of laser energy is directed to the plaque 42 to remove a small portion. The guidewire 30 is then pushed a little deeper through the plaque 42 and another small laser pulse is fired through the fiber optic rods to the plaque 42 to remove a small portion thereof. These steps are repeated until a tunnel is bored completely through the occlusion formed by the plaque 42. Since the tunnel is incrementally bored by small laser pulses, the risk of perforating the wall of the blood vessel 40 is substantially reduced.

Figure 6:
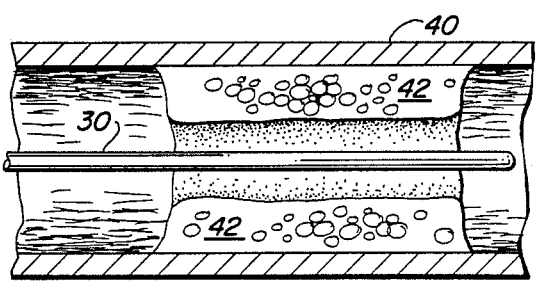
FIG. 6 illustrates a guidewire within the through tunnel of FIG. 5.

After the tunnel through the occlusion is formed, the catheter 30 is removed from the blood vessel 40 and the guidewire 30 left in place as shown in FIG. 6. As shown in FIG. 7, if further opening of the occlusion is required, a balloon catheter 50 is inserted into the blood vessel 40 along the guidewire 30. The balloon catheter 50 has a distal end dimensioned to pass freely along the blood vessel 40 and a proximal end (not shown) adapted to extend outside the human body during use. The balloon catheter is provided with a longitudinal lumen extending generally along the center of the balloon catheter 50. The balloon catheter 50 also has an expandable zone 52 near its distal end. The expandable zone 52 of the balloon catheter 50 is guided into the tunnel through the plaque 42. As shown in FIG. 8, the expandable zone 52 of the balloon catheter 50 is expanded to dilate the wall of the blood vessel 40 to open the occlusion. The expandable zone 52 is then contracted and the balloon catheter 50 removed from the blood vessel 40. As shown in FIG. 8, the plaque 42 is not actually removed from the blood vessel 40 but is spread over the wall of the blood vessel 40. The wall of the blood vessel 40 remains partially dilated and so the effect of the occlusion is removed.

Reference is made to FIG. 10 which illustrates a distal end of another embodiment of a laser catheter 60. The fiber optic rods 62 are shown with 30° cleavage planes for aiming the coherent radiation. The path of the coherent radiation from the fiber optic rods 62 is denoted with broken lines. The 30° cleavage planes create a tight overall divergence and a close cross-over of the central rays. As shown, the central rays focus coherent radiation on the tip of the guidewire 70 to heat the guidewire 70. The heated guidewire is then pushed against the plaque to burn a tunnel through the occlusion. Preferably, the guidewire 70 is formed from a coherent radiation absorptive heat conductive material.

FIG. 11 shows the catheter 60 of FIG. 10 focusing coherent radiation on an occlusion 75 within a blood vessel 78, rather than focusing the radiation on the guidewire 70. By convergently focusing the radiation, a central zone of the occlusion 75 is ablated.

Reference is now made to FIG. 12 where a cross-sectional view of another embodiment of a laser catheter 80 is shown. In this embodiment, instead of having a plurality of fiber optic rods the catheter 80 only has one fiber optic rod 82 formed with a longitudinal lumen 84 at its center. The lumen 84 is dimensioned to allow the catheter to pass over a guidewire (not shown). The operation of the catheter of FIG. 11 is similar to the operation of the catheter shown in FIGS. 1 and 2.

While the principles of the invention have now been made clear in an illustrative embodiment, there will become obvious to those skilled in the art many modifications in structure, arrangement, components, and materials used in the practice of the invention and otherwise which are particularly adapted for specific operating requirements without departing from those principles. The appended claims are therefore intended to cover and embrace any such modifications.

I claim:

1. Apparatus for opening an occlusion which is in a passageway in the human body, said apparatus comprising:
   (a) a catheter with a distal end adapted to pass freely along the passageway, said catheter including a longitudinal lumen and having a proximal end adapted to extend outside the human body during use;
   (b) a source of coherent radiation;
   (c) means for coupling said source of coherent radiation to said proximal end of said catheter;
   (d) means along said catheter for transmitting said coherent radiation from said source to said distal end to permit said coherent radiation to be directed against an occlusion in the passageway to bore a tunnel through the occlusion so that a catheter may pass through the tunnel;
   (e) a guidewire dimensioned to pass through said lumen for guiding said distal end of said catheter to the occlusion; and
   (f) means at said distal end for focusing said coherent radiation onto said guidewire.

2. The apparatus recited in claim 1 wherein said transmitting means comprises plural, flexible fiber optic rods extending generally longitudinally along said catheter and generally parallel with said lumen.

3. The apparatus recited in claim 2 wherein said lumen extends generally along the center of said catheter, with said fiber optic rods disposed about said lumen.

4. The apparatus recited in claim 2 further comprising means at said distal end for focusing coherent radiation passing through said fiber optic rods.

5. The apparatus recited in claim 4 further comprising means for convergently focusing said coherent radiation at a central zone of the occlusion.

6. The apparatus recited in claim 1 wherein said guidewire at said distal end comprises a coherent radiation absorptive, heat conductive material.

7. The apparatus recited in claim 6 wherein said guidewire comprises a flexible metallic guidewire.

8. Apparatus for opening an occlusion which is in a passageway in the human body, said apparatus comprising:
(a) a catheter with a distal end adapted to pass freely along the passageway, said catheter including a longitudinal lumen and having a proximal end adapted to extend outside the human body during use;
(b) a source of coherent radiation;
(c) means for coupling said source of coherent radiation to said proximal end of said catheter;
(d) heat conductive means adjacent to said distal end of said catheter for receiving coherent radiation;
(e) means along said catheter for transmitting coherent radiation from said source to said distal end to permit said coherent radiation to be directed against said heat conductive means to bore a tunnel through an occlusion in the passageway; and
(f) means including a guidewire dimensioned to pass through the lumen for guiding said distal end of said catheter to the occlusion, said guidewire having said heat conductive means at a distal extremity thereof.

9. The apparatus recited in claim 8 wherein said transmitting means comprises plural, flexible fiber optic rods extending generally longitudinally along said catheter and generally parallel with said lumen.

10. The apparatus cited in claim 9 wherein said lumen extends generally along the center of said catheter, with said fiber optic rods disposed about said lumen.

11. The apparatus recited in claim 9 further comprising means at said distal end for focusing coherent radiation passing through said fiber optic rods.

12. The apparatus recited in claim 11 further comprising means for convergently focusing said coherent radiation onto said heat conductive means.

13. Apparatus for opening an obstructed tubular passageway in the human body, said apparatus comprising:
(a) a first catheter including a first longitudinal lumen with a distal end adapted to pass freely along the tubular passageway, said catheter having a proximal end adapted to extend outside the human body during use;
(b) a source of coherent radiation;
(c) means for coupling said source of coherent radiation to said proximal end of said first catheter;
(d) a second catheter including a second longitudinal lumen and having a distal end adapted to pass freely along the tubular passageway, a proximal end adapted to extend outside the human body during use, and a peripheral elastic expandable zone spaced from the distal end of said second catheter;
(e) means including a guidewire dimensioned to pass through both of said longitudinal lumens for guiding said distal end of said first catheter to an obstruction in the tubular passageway and for guiding said distal end of said second catheter to the location of the obstruction after removal of said first catheter from the tubular passageway;
(f) means along said first catheter for transmitting coherent radiation from said source to said distal end of said first catheter to permit said coherent radiation to be directed against an obstruction to bore a tunnel through the obstruction so that said expandable zone of said second catheter may pass through the tunnel; and
(g) means for expanding said expandable zone when said expandable zone is in the tunnel through the obstruction.

14. The apparatus recited in claim 13 wherein said transmitting means comprises plural, flexible fiber optic rods extending generally longitudinally along said first catheter and generally parallel with said first lumen.

15. The apparatus recited in claim 14 wherein said first lumen extends generally along the center of said first catheter, with said fiber optic rods disposed about said first lumen.

16. The apparatus recited in claim 15 further comprising means at said distal end of said first catheter for focusing coherent radiation passing through said fiber optic rods.

17. The apparatus recited in claim 13 wherein said transmitting means comprises a flexible fiber optic rod extending generally longitudinally along said first catheter and generally parallel with said first lumen.

18. A method for treating a restriction in an artery of a patient caused by atherosclerotic plaque, comprising the steps of:
passing a guidewire along the patient's arterial passageways to said restriction;
providing an optical energy catheter having a lumen dimensioned to receive said guidewire so that said optical energy catheter can be passed along said guidewire to said restriction;
providing a balloon catheter having a lumen dimensioned to receive said guidewire so that said balloon can be passed along said guidewire to said restriction; and
placing said guidewire in said restriction while sequentially passing said catheters along said guidewire to treat said restriction.

19. A method for opening an obstructed blood vessel in the human body, comprising the steps of:
(a) providing a first catheter having a first longitudinal lumen and having a distal end dimensioned to pass freely along the obstructed blood vessel and a proximal end adapted to extend outside the human body;
(b) providing a source of coherent radiation;
(c) coupling the source of coherent radiation to the proximal end of the first catheter;
(d) providing a guidewire dimensioned to pass along the longitudinal lumen and extending said guidewire through the blood vessel to an obstruction therein;

(e) thereafter guiding the distal end of the first catheter to the obstruction by passing the first catheter along said guidewire;

(f) transmitting coherent radiation from the source to the distal end of the first catheter to permit radiation to be directed against the obstruction to bore a tunnel through the obstruction;

(g) removing the first catheter from the blood vessel;

(h) leaving the guidewire in the blood vessel during and after the removal of the first catheter;

(i) providing a second catheter having a second longitudinal lumen dimensioned to pass over said guidewire and having a distal end adapted to pass freely along the blood vessel, a proximal end adapted to extend outside the human body, and a peripheral elastic expandable zone spaced from the distal end thereof;

(j) guiding the expandable zone of the second catheter along the guidewire into the tunnel through the obstruction;

(k) expanding the expandable zone of the second catheter to increase the size of the tunnel through the obstruction; and (l) removing the second catheter and the guidewire from the blood vessel.

20. The method recited in claim 19, comprising the further steps of sequentially transmitting radiation from said distal end of said first catheter to open a portion of the obstruction, then extending said guidewire into the opened portion and thereafter repeating the radiation transmitting and guidewire extending steps.--

21. A method for treating an occlusion in a passageway within the human body, comprising the steps of:

(a) passing a flexible guidewire into the body and along the passageway until a distal extremity of the guidewire is adjacent the occlusion;

(b) passing a first, optically transmissive catheter along the guidewire until a distal end of the first catheter is adjacent the occlusion;

(c) transmitting optical energy along the first catheter and emitting radiation from the distal end thereof to at least partially open the occlusion;

(d) extending the guidewire through the opening in the occlusion;

(e) removing the first catheter from the passageway while maintaining the guidewire in place within the opening in the occlusion;

(f) passing a second, expandable catheter along the guidewire and into the opening of the occlusion;

(g) expanding said second catheter in the opening of the occlusion to increase the size of the opening; and thereafter (h) removing said second catheter and said guidewire from the passageway.--

22. The method recited in claim 21 wherein said optical transmitting and guidewire extending steps comprise sequential steps of (i) energizing said first catheter to remove a portion of the occlusion, (ii) extending the distal end of the guidewire into the area of the removed portion, and thereafter repeating steps (i) and (ii).

23. A method for opening an obstructed tubular passageway in the human body, comprising the steps of:

(a) providing a first catheter having a first longitudinal lumen and having a distal end adapted to pass freely along the tubular passageway and a proximal end adapted to extend outside the human body;

(b) providing a source of coherent radiation;

(c) coupling the source of coherent radiation to the proximal end of the first catheter;

(d) providing a guidewire having a heat conductive means at the distal end thereof, and dimensioned to pass along the longitudinal lumen and extending said guidewire through the blood vessel to an obstruction therein;

(e) thereafter guiding the distal end of the first catheter to the obstruction by passing the first catheter along the guidewire;

(f) transmitting coherent radiation from the source to the distal end of the first catheter to permit radiation to be directed at the heat conductive means adjacent to the distal end of the first catheter to heat the heat conductive means;

(g) placing the heat conductive means against the obstruction to bore a tunnel through the obstruction;

(h) removing the first catheter from the tubular passageway;

(i) providing a second catheter having a second longitudinal lumen and having a distal end dimensioned to pass freely along the tubular passageway, a proximal end adapted to extend outside the human body and a peripheral elastic expandable zone spaced from the distal end;

(j) guiding the expandable zone of the second catheter along the guidewire and into the passageway through the obstruction;

(k) expanding the expandable zone of the second catheter to increase the size of the tunnel through the obstruction; and (l) removing the second catheter and the guidewire from the tubular passageway.

* * * * *